United States Patent [19]

Willis et al.

[11] 4,233,460

[45] Nov. 11, 1980

[54] ALKOXYALKANOIC ACID PREPARATION

[75] Inventors: Carl L. Willis; Lynn H. Slaugh, both of Houston, Tex.

[73] Assignee: Shell Oil Company, Houston, Tex.

[21] Appl. No.: 35,871

[22] Filed: May 3, 1979

[51] Int. Cl.² .............................................. C07C 51/26
[52] U.S. Cl. .................................... 562/537; 560/131; 560/180; 562/418; 562/525; 562/526
[58] Field of Search ............... 562/537, 525, 526, 418; 560/131, 180

[56] References Cited

U.S. PATENT DOCUMENTS

| | | | |
|---|---|---|---|
| 3,342,858 | 9/1967 | Fuhrmann et al. | 562/537 |
| 3,929,873 | 12/1975 | Gammans | 562/537 |

*Primary Examiner*—Vivian Garner
*Attorney, Agent, or Firm*—Howard W. Haworth

[57] ABSTRACT

An extremely mild, oxidative process for converting alkoxyalkanols to the corresponding acids is disclosed which comprises reacting the alcohol with an alkali metal hydroxide and tert-butyl hydroperoxide in the presence of a catalytic amount of palladium.

3 Claims, No Drawings

ALKOXYALKANOIC ACID PREPARATION

BACKGROUND OF THE INVENTION

1. Field of the Invention

This invention relates to the production of alkoxyalkanoic acids by the oxidation of the corresponding alcohols.

2. Description of the Relevant Art

Alkoxyalkanoic acids find use as anionic detergents. These acids being composed of only the elements C, H and O do not pose the environmental problems that other detergents containing heteroatoms such as N, S, and P pose. Commercially, the alkoxyalkanoic acids are prepared in a two-step process of first reacting an alkoxyalkanol with sodium and then reacting the resultant ethoxide with the sodium salt of chloroacetic acid. A one-step process avoiding the use of chloroacetic acid and providing a NaCl free product would be of significant commercial interest.

Japanese Pat. No. 50-96516 issued July 31, 1975, discloses a process for the preparation of carboxylic acid salts by the liquid phase dehydrogenation of alcohols with caustic alkali in the presence of precious metal catalysts, including palladium. This process uses a relatively high temperature, 100°–270° C. These high temperatures can degrade the ether linkages especially in the highly ethoxylated alcohols.

In U.S. Pat. No. 3,342,858, issued Sept. 19, 1967 discloses a lower temperature process using a platinum catalyst. This process uses an oxygen containing gas as the oxidant. This process presents all the problems attendant with two-phase operations such as gaseous diffusion limitations, additional equipment such as compressors needed to process the gas phase. A process operating substantially in the liquid phase overcomes many of these problems of gas-liquid phase reactions.

SUMMARY OF THE INVENTION

This instant process is an extremely mild, low temperature oxidative process for converting alkoxyalkanols to alkoxyalkanoic acids by reacting the alcohols with an alkali metal hydroxide and tertiary butyl hydroperoxide in the presence of a catalytic amount of palladium. This process minimizes degradation products, provides high conversions of the alcohol and tert-butyl hydroperoxide with high selectivity to the acid salt. The process operates in the liquid phase, avoiding the problems of two-phase operation. The process is particularly suited to the detergent range, ethoxylate alcohols.

DESCRIPTION OF THE PREFERRED EMBODIMENTS

The present process converts alkoxyalkanols of the formula:

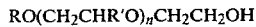

wherein R is an alkyl group, preferably of 1 to about 22; more preferably of about 11 to about 18 carbon atoms, R' is hydrogen or methyl or mixtures thereof (on the individual molecule) and n is an integer of from 1 to about 12, preferably of from about 2 to about 9, to the corresponding alkoxyalkanoic acids of the formula:

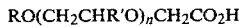

by reacting the alcohols with a hydroxide and tert-butyl hydroperoxide in the presence of a palladium catayst. The R group can be substituted with any substituent which does not interfere with the oxidation of the hydroxy group. Such substituents include —OR", —CH$_3$, —COOH, —CO NH$_2$ and —COOR" wherein R" is an alkyl or aryl group. The process is particularly suited to detergent range ethoxylated, or propoxylated alcohols with alkyl chains (R) of about 8 to about 20, preferably of about 11 to about 18. The R' groups on an individual molecule can be hydrogen, methyl or mixtures thereof. For example, straight ethoxylates, straight propoxylates and mixed ethoxylate-propoxylate detergent alcohols are commercially available. The number of such alkoxyate groups, (CH$_2$CH R'0), range from 1 to about 12. Commercially, detergent range ethoxylate alcohols are available with an average of 3, 7, 9 and 12 ethoxylate units per molecule. Others can readily be prepared. The process is thought to be produced by the following reaction:

$$RO(CH_2CH\ R'O)_nCH_2CH_2OH + NaOH + \quad (1)$$
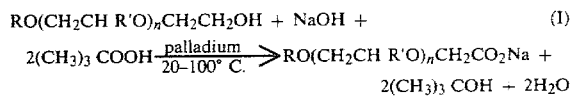
$$2(CH_3)_3 COH + 2H_2O$$

The acid product is produced in the form of the alkali metal salt and it is to be understood that the term "acid" as used herein is intended to include the salt forms as well as the free acid form.

Although NaOH is shown in equation I as the base utilized, any alkali metal hydroxide is suitable, i.e. lithium, sodium, potassium, rubidium or cesium. A strong base, such as the alkali metal hydroxide, is needed. When weaker bases such as NaHCO$_3$ were used, no reaction occured. At least one equivalent of base for each equivalent of alcohol reacted will need be provided. It has been found that maximum conversion is obtained when a slight excess of strong base is present during the reaction. This requirement for a slight excess of strong base affects the manner of base addition. As one equivalent of base is consumed per equivalent of acid product formed, the base must be added at least as fast as oxidation is proceeding in order to maintain an excess. Further, unreacted tert-butyl hydroperoxide also reacts with the base to form the base salt thereof so that if the tert-butyl hydroperoxide is added to the reaction faster than it is consumed, the addition of base must be adjusted to maintain an excess. In the limit, if all the tert-butyl hydroperoxide (2 equivalents) is added at the start of the reaction, then slightly more than two equivalents of base must be added at the outset to ensure an excess of hydroxide. This approach will leave an excess of base (1 equivalent) in the final product. In general it is preferred to add one equivalent of base to the starting mixture and meter the tert-butyl hydroperoxide into the reaction at slightly less than the maximum rate at which it could be consumed by the catalyst. This technique would leave no excess base in the final product. Alternately the base and hydroperoxide to be simultaneously metered into the reactor, with the rate of injection of hydroperoxide slightly less than its consumption and the base adjusted to provide a slight excess. The rates can readily be determined by routine experimentation.

The catalyst utilized is heterogeneous palladium metal, either the metal alone or supported on a suitable support. Suitable supports are those which are inert to the reaction conditions. Examples of supports suitable for certain reaction conditions are carbon, alumina, clay, silica, pumice, magnesia, zirconia, titania, etc. Some of the supports, such as alumina and silica are sensitive to base concentrations, i.e. dissolution of the support in high hydroxide concentrations. These types of supports can be used only when the excess hydroxide is low. Carbon is a highly desirable support since it is neutral to all reaction conditions. Satisfactory commercial catalysts containing up to 10% wt. of palladium on carbon are readily available and quite suitable for use in the process. While the unsupported catalyst is suitable, it is less preferable to the supported catalysts since more of the expensive palladium metal is required to achieve the same results as with the supported catalysts. The catalysts are frequently reduced in hydrogen prior to use to assure that the palladium is in the reduced state. Amounts of palladium to reactant alcohol are not critical, but the amount of palladium present can affect the rates. Preferably, the mole ratio of palladium to reactant alcohol is greater than 1/1000, more preferably 1/100.

The reaction is conducted under relatively mild conditions with good results being obtained using a temperature of about 20°–100° C., preferably from about 40° to about 80° C. There are no particular pressure requirements in the process since it is liquid phase. Atmospheric pressure is most convenient.

The reaction may be carried out in a solvent medium. The preferred solvent for the system is water. Water is a coproduct of the oxidation reaction, and its presence has no effect on the oxidative process. When water is used as a solvent, it is preferably used in amounts up to about 20% by weight.

The reaction product can be purified by a number of conventional procedures. One method is acidifying the reaction product with a strong inorganic acid such as HCl to convert the product to its acid form, adding a salt such as sodium sulfate to increase the number of ions in water and thus increasing the selective solubility of the product in ether and then extracting the alkoxyalkanoic acid with ether. Next, the ether is evaporated and the acid product is dried, as by drying with a salt such as sodium sulfate or by azeotropic distillation with benzene, etc. Further purification can be effected by fractional distillation.

The yields of the alkoxyalkanoic acid obtained by this invention are excellent with, under optimum conditions, conversion of the alcohol of 80–95% being obtained with selectives in excess of 95 mol % obtained.

The process of this invention will be further described by the following illustrative embodiments which are provided for illustration and are not to be construed as limiting the invention.

ILLUSTRATIVE EMBODIMENTS

In the following examples, the starting alcohol was a SHELL NEODOL® ethoxylate 23-3T alcohol which was prepared by ethoxylating a mixture of $C_{12}$ and $C_{13}$ substantially straight chain alcohols ($C_{12}$:$C_{13}$~40:60) to an ethoxylate alcohol having about 3 ethylene oxide units per molecule and then topping off the unreacted alcohols and lower ethoxylates so that the final product has about five ethylene oxide units per molecule.

The tertiary butyl hydroperoxide was t-Butyl Hydroperoxide 90 from Lucidol Division of Pennwalt Corporation which is a solution of tert-butyl hydroperoxide 90% in tert-butyl alcohol (10%). The material was 10 molal with a density of 0.9 g/ml.

The NaOH used was pelletized "Baker Analyzed" Reagent Grade (97.7%).

Conversion (basis alcohol) is calculated as the moles of alkoxyalkanoic acid divided by moles of starting alcohols times 100 (%).

Conversion (basis hydroperoxide) is calculated as moles of hydroperoxide consumed divided by moles at start times 100 (%).

Selectivity (basis alcohol) is calculated as the moles of alkoxyalkanoic acid found divided by total moles of carboxylic acid found times 100 (%).

Selectivity (basis hydroperoxide) is calculated as twice the moles of alkoxyalkanoic acid found divided by moles of hydroperoxide used times 100 (%).

The following abbreviations are used in the examples.
TBHP for tertiary butyl hydroperoxide
TBA for tertiary butyl alcohol
AEA for alkylethoxyl acid (alkoxyalkanoic acid).

ILLUSTRATIVE EMBODIMENT I

In a typical experiment, a batch reactor at 60° C. was charged with 2 grams (g) of $H_2O$ and 2.0 g (0.050 mol) of NaOH under an argon atmosphere. After NaOH dissolution, 20.6 (0.050 mol) of NEODOL® ethoxylate 23-3T was added to the reactor as vigorous mechanical stirring was initiated. This mixture was charged with 1.1 g (0.0010 mol) of a commercial Pd on powdered charcoal catalyst (10 w% Pd loaded, Alpha Products). Two equivalents (11 ml, 0.10 mol) of a 90 w% solution of TBHP in TBA were added to the slurry at a rate of 1.3 equivalents per hour (7 ml/hr). The reaction was stirred for an additional 0.4 hour after all of the TBHP has been added. An aliquot of the product was removed centrifuged to remove the bulk of the catalyst, and analyzed with the following results.

| Detergent acid (AEA) | 0.037 mol |
|---|---|
| Non-detergent carboxylic acid | 0.002 mol |
| Unconsumed TBHP | 0.014 mol |

Several parameters were varied and the results are shown in Table I. Experiments I-1 thru I-4 show that the presence of up to 20% weight of water in the reaction medium has little effect.

Experiments I-5 thru I-6 show a temperature optimum at about 40°–80° C.

Experiments I-9 thru I-12 show the effect of NaOH. The use of less than stoichiometric quantities of NaOH gives poor results whereas slightly greater provides an advantage. Experiment I-13 shows the CsOH is equivalent to NaOH. Experiment I-14 shows that a weak base, $NaHCO_3$ is ineffective.

TABLE I

PARAMETER OPTIMIZATION
FOR THE PD/C OXIDATION
OF NEODOL® ETHOXYLATE 23-3T WITH TBHP[1]

$$RO(CH_2CH_2O)_xCH_2CH_2OH + 2\ TBHP + NaOH \xrightarrow{Pd/C^2}$$
$$RO(CH_2CH_2O)_xCH_2CO_2Na + 2TBA + 2H_2O$$

| Expt. No. | | NEODOL® Ethoxylate 23-3T | |
|---|---|---|---|
| | | Conversion[5] (Mol %) | Selectivity[6] (Mol %) |
| | $[H_2O]^3$ (Wt %) | | |
| I-1 | 0 | 75 | 98 |
| I-2 | 5 | 66 | 94 |
| I-3 | 10 | 80 | 94 |

TABLE I-continued
PARAMETER OPTIMIZATION FOR THE PD/C OXIDATION OF NEODOL® ETHOXYLATE 23-3T WITH TBHP[1]

$$RO(CH_2CH_2O)_xCH_2CH_2OH + 2\ TBHP + NaOH \xrightarrow{Pd/C[2]}$$
$$RO(CH_2CH_2O)_xCH_2CO_2Na + 2TBA + 2H_2O$$

| Expt. No. | | | |
|---|---|---|---|
| I-4 | 20 | 86 | 97 |
| | Temperature (°C.) | | |
| I-5 | 20 | 47 | 85 |
| I-6 | 40 | 72 | 92 |
| I-7 | 60 | 92 | 87 |
| I-8 | 80 | 73 | 93 |
| I-9 | 100 | 69 | 88 |
| | NaOH (Equiv.) | | |
| I-10 | 0 | 0 | — |
| I-11 | 0.5 | 39 | 89 |
| I-12 | 1.0 | 74 | 95 |
| I-13 | 1.4 | 86 | 97 |
| I-14 | 2.0 | 83 | 91 |
| I-15 | 1.0 (CsOH) | 56 | — |
| I-16 | 1.0 (NaHCO₃) | 0 | — |
| | Pd/Alcohol (Mol %) | | |
| I-17 | 0 | 4 | 9 |
| I-18 | 1.0 | 56 | 85 |
| I-19 | 2.0 | 66 | 94 |
| I-20 | 4.0 | 68 | 89 |
| | TBHP (Equiv.) | | |
| I-21 | 0 (O₂) | 0 | — |
| I-22 | 1.0 | 51 | 94 |
| I-23 | 1.0 (O₂) | 54 | 100 |
| I-24 | 1.5 | 70 | 94 |
| I-25 | 2.0 | 92 | 87 |
| | Rate of TBHP Addition (mmol/hr) | | |
| I-26 | 200 | 42 | 83 |

| | TBHP | | |
|---|---|---|---|
| Expt. No. | Conversion[7] (Mol %) | Selectivity[8] (Mol %) | Rate[4] (mol/mol/hr) |
| I-1 | 88 | 86 | 19 |
| I-2 | 93 | 71 | 17 |
| I-3 | 94 | 86 | 20 |
| I-4 | 94 | 92 | 22 |
| I-5 | 79 | 60 | 12 |
| I-6 | 94 | 77 | 18 |
| I-7 | 98 | 96 | 23 |
| I-8 | 95 | 78 | 18 |
| I-9 | 99 | 70 | — |
| I-10 | 30 | 0 | 0 |
| I-11 | 72 | 55 | 10 |
| I-12 | 93 | 80 | 19 |
| I-13 | 100 | 87 | 22 |
| I-14 | 98 | 91 | 21 |
| I-15 | 72 | 78 | 14 |
| I-16 | 67 | 0 | 0 |
| I-17 | 71 | 5 | — |
| I-18 | 86 | 66 | 28 |
| I-19 | 93 | 71 | 17 |
| I-20 | 85 | 80 | 9 |
| I-21 | — | — | 0 |
| I-22 | 94 | 100 | — |
| I-23 | 100 | 100 | 27 |
| I-24 | 96 | 99 | — |
| I-25 | 98 | 96 | 23 |
| I-26 | 92 | 46 | 46 |

[1]Unless otherwise indicated, the experiment consisted of adding 100 mmol of TBHP (90 wt % in TBA) over a period of 90 min. to 20.6 g (50 mmol) of NEODOL® ethoxylate 23-3T containing 2 g (50 mmol) of NaOH (60° C.) (total reaction time = 2 hr). For all runs except I-17, I-18 and I-20, 1 mmol of Pd was used (2 mol % basis alcohol).
[2]All experiments employed a commercial 5 wt % Pd-on-powdered-charcoal catalyst except I-9, -11, -12, -13, -14, -17, -23 where a 10 wt % loaded material was used.
[3]Wt % H₂O added to alcohol feed (i.e., 1 g H₂O = 5 wt %).
[4]Rate = mol AEA/mol catalyst/hr. These rates represent lower limits only.
[5]Conv. = (mmol AEA found ÷ 50 mmol starting alcohol) 100.
[6]Select. = (mmol AEA found ÷ mmol total carboxylic acid found) 100.
[7]Conv. = (mmol TBHP consumed ÷ mmol starting TBHP) 100.
[8]Select. = ((2 × mmol AEA found) ÷ mmol TBHP consumed) 100.

Experiments I-17 thru I-20 show the effects of palladium to alcohol (starting) ratio. At higher palladium to alcohol ratios, the TBHP was used more effectively hence higher alcohol conversions were attained, but at a higher catalyst cost.

Experiments I-21 thru I-25 show the relationship between the amount of TBHP added to the reaction and the yield of AEA up to the stoichiometric limit (2 equivalents). In an attempt to circumvent the TBHP requirements, an experiment was conducted TBHP deficient (50% of the theoretical amount) with an oxygen atmosphere (Exp. I-23). The added oxygen did not augment the total oxidizing ability of the medium. Experiment I-21 completely substituted oxygen for TBHP with no effect noted.

ILLUSTRATIVE EMBODIMENT II

A series of catalysts were screened utilizing the general procedures of Illustrative Embodiment I and the results are shown in Table II. While some of the metals such as Pt, Ir and Ru showed some activity, the Pd was far superior.

TABLE II
EFFECT OF CATALYST ON OXIDATION OF NEODOL® ETHOXYLATE 23-3T WITH TBHP[1]

$$RO(CH_2CH_2O)_xCH_2CH_2OH + 2\ TBHP + NaOH \rightarrow$$
$$RO(CH_2CH_2O)_xCH_2CO_2Na + 2TBA + 2H_2O$$

| Expt. No. | Catalyst[2] | Catalyst/ Substrate[3] (Mol %) | NEODOL® Ethoxylate 23-3T Conversion[5] (Mol %) | Selectivity[6] (Mol %) |
|---|---|---|---|---|
| II-1 | 10 Wt % Pt/C | 1 | 17 | 77 |
| II-2 | 10 Wt % Pt/Al₂O₃ | 1 | 0 | — |
| II-3 | 10 Wt % Ni/C | 2 | 2 | 14 |
| II-4 | 5 Wt % Rh/C | 2 | 2 | 19 |
| II-5 | 33 Wt % Ir/Al₂O₃ | 1 | 7 | 28 |
| II-6 | 5 Wt % Ru/C | 2 | 8 | 34 |
| II-7 | 5 Wt % Re/C | 1 | 3 | 11 |
| II-8 | 10 Wt % Mo/Al₂O₃ | 2 | 5 | 25 |
| II-9 | 5 Wt % Pd/Al₂O₃ | 2 | 13 | 65 |
| II-10 | 5 Wt % Pd/C | 2 | 66 | 94 |
| II-11 | No metal added | 0 | 4 | 9 |

| | TBHP | | |
|---|---|---|---|
| Expt. No. | Conversion[7] (Mol %) | Selectivity[8] (Mol %) | Rate[4] (mol/mol/hr) |
| II-1 | 96 | 17 | 9 |
| II-2 | 35 | 0 | 0 |
| II-3 | 60 | 3 | 1 |
| II-4 | 79 | 3 | 1 |
| II-5 | 50 | 14 | 4 |
| II-6 | 84 | 10 | 2 |
| II-7 | 67 | 4 | 2 |
| II-8 | 48 | 10 | 1 |
| II-9 | 80 | 16 | 3 |
| II-10 | 93 | 71 | 17 |

TABLE II-continued

EFFECT OF CATALYST
ON OXIDATION OF NEODOL® ETHOXYLATE
23-3T WITH TBHP[1]

$RO(CH_2CH_2O)_xCH_2CH_2OH + 2\ TBHP + NaOH \rightarrow$
$RO(CH_2CH_2O)_xCH_2CO_2Na + 2TBA + 2H_2O$

| II-11 | | 5 |
|---|---|---|

[1]100 mmol of TBHP (90 Wt % in TBA) was added over a period of 90 min. to 20.6 g (50 mmol) of NEODOL ® Ethoxylate 23-3T
[2]Commercial catalyst on powdered support (except Ir/Al$_2$O$_3$ and Mo/Al$_2$O$_3$ which were granular)
[3]Moles of metal per mole of alcohol
[4]Rate = mol AEA/mol catalyst/hr. These rates represent lower limits only
[5]Conv. = (mmol AEA found ÷ mmol starting alcohol) 100.
[6]Select. = (mmol AEA found ÷ mmol total carboxylic acid found) 100
[7]Conv. = (mmol TBHP consumed ÷ mmol starting TBHP) 100
[8]Select. = ((2 × mmol AEA found) ÷ mmol TBHP consumed) 100.

ILLUSTRATIVE EMBODIMENT III

A vertical fixed-bed reactor was utilized in this experiment. The reactor was water-jacketed to provide the appropriate reactor temperature. The catalyst bed was loaded with 50 g (1.4 mmol) of a 0.3 wt% Pd- on 20×40 mesh granular-charcoal catalyst (Oxy-Catalyst, Lot 4234-A). A slurry containing NEODOL ® ethoxylate 23-3T (82.4 g, 200 mmol), NaOH (13.2 g, 330 mmol), and H$_2$O (12 g) was introduced into the top of the catalyst bed via a recycle pump. The reactor was equilibrated at 60° C. and the recycle pump adjusted to a downward flow of 7 ml/ml catalyst/hr. Two equivalents of TBHP (400 mmol) were added to the top of the catalyst bed at the rate of 26 mol/mol Pd/hr (LHSV=0.05). An aliquot of the final product was removed and analyzed with the following results:

| | |
|---|---|
| Conversion (basis alcohol) | 83% |
| Selectivity (basis alcohol) | 93% |
| Conversion (basis TBHP) | 100% |
| Selectivity (basis TBHP) | 77% |
| Rate (mol AEA/mol Pd/hr) | 10 |

What is claimed is:

1. A process for preparing an alkoxyalkanoic acid of the formula:

$$RO(CH_2CHR'O)_nCH_2CO_2H$$

wherein R is an alkyl group of 1 to about 22 carbon atoms, R' is hydrogen or methyl or a mixture thereof (on the individual molecule) and n is an integer of from 1 to about 12 by reacting the corresponding alkoxyalkanol with tertiary butyl hydroperoxide and an alkali metal hydroxide in the liquid phase at a temperature of about 20° to about 100° C. in the presence of a catalytically effective amount of palladium metal while maintaining during the reaction an excess of the alkali metal hydroxide.

2. The process of claim 1 wherein R is an alkyl group of about 11 to about 18 carbon atoms and n is an integer from about 2 to about 9.

3. The process of claim 1 or 2 wherein the molar ratio of palladium to alkoxyalkanol is greater than 1/1000.

* * * * *